United States Patent [19]

Berg

[11] Patent Number: 5,693,194
[45] Date of Patent: Dec. 2, 1997

[54] SEPARATION OF BUTYRALDEHYDE FROM ETHANOL BY EXTRACTIVE DISTILLATION

[76] Inventor: Lloyd Berg, 1314 S. Third Ave., Bozeman, Mont. 59715

[21] Appl. No.: 753,410

[22] Filed: Nov. 25, 1996

[51] Int. Cl.⁶ .................................. B01D 3/40; C07C 45/83
[52] U.S. Cl. ............................... 203/57; 203/58; 203/60; 203/62; 203/63; 203/64; 203/65; 203/68; 568/492; 568/913
[58] Field of Search ......................... 203/57, 58, 60, 203/62, 63, 64, 65, 68, 67, DIG. 13; 568/492, 890, 913

[56] References Cited

U.S. PATENT DOCUMENTS

| | | | |
|---|---|---|---|
| 3,481,837 | 12/1969 | Johnson, Jr. et al. | 203/46 |
| 3,960,672 | 6/1976 | Ester | 203/18 |
| 4,382,843 | 5/1983 | Black | 203/70 |
| 4,383,893 | 5/1983 | Kaibel et al. | 568/913 |
| 4,428,798 | 1/1984 | Zudkevitch et al. | 203/65 |
| 4,455,198 | 6/1984 | Zudkevitch et al. | 203/62 |
| 4,986,885 | 1/1991 | Driscoll et al. | 568/913 |
| 5,580,427 | 12/1996 | Berg | 203/57 |

FOREIGN PATENT DOCUMENTS

| | | | |
|---|---|---|---|
| 0116534 | 5/1987 | Japan . | |
| 0196532 | 8/1988 | Japan . | |
| 0667134 | 2/1952 | United Kingdom | 203/68 |
| 0682487 | 11/1952 | United Kingdom | 203/63 |

*Primary Examiner*—Virginia Manoharan

[57] ABSTRACT

Butyraldehyde cannot be separated from ethanol by conventional distillation or rectification because they form a minimum boiling azeotrope. Butyraldehyde can be readily separated from ethanol by extractive distillation. Effective agents are 2-propanol, m-xylene and dimethylsulfoxide.

2 Claims, No Drawings

SEPARATION OF BUTYRALDEHYDE FROM ETHANOL BY EXTRACTIVE DISTILLATION

FIELD OF THE INVENTION

This invention relates to a method for separating butyraldehyde from ethanol using certain organic liquids as the agent in extractive distillation.

DESCRIPTION OF PRIOR ART

Extractive distillation is the method of separating close boiling compounds from each other by carrying out the distillation in a multiplate rectification column in the presence of an added liquid or liquid mixture, said liquid(s) having a boiling point higher than the compounds being separated. The extractive agent is introduced near the top of the column and flows downward until it reaches the stillpot or reboiler. Its presence on each plate of the rectification column alters the relative volatility of the close boiling compounds in a direction to make the separation on each plate greater and thus require either fewer plates to effect the same separation or make possible a greater degree of separation with the same number of plates. The extractive agent should boil higher than any of the close boiling liquids being separated and not form minimum azeotropes with them. Usually the extractive agent is introduced a few plates from the top of the column to insure that none of the extractive agent is carried over with the lowest boiling component. This usually requires that the extractive agent boil about twenty Celcius degrees or more higher than the highest boiling component.

At the bottom of a continuous column, the less volatile components of the close boiling mixtures and the extractive agent are continuously removed from the column. The usual methods of separation of these two components are the use of another rectification column, cooling and phase separation, or solvent extraction.

The usual method of evaluating the effectiveness of extractive distillation agents is the change in relative volatility of the compounds to be separated. Table 1 shows the degree of separation or purity obtainable by theoretical plates at several relative volatilities. Table 1 shows that a relative volatility of at least 1.2 is required to get an effective separation by rectification.

TABLE 1

Effect of Relative Volatility on Theoretical Stage Requirements

| Separation Purity, Both Products (Mole Fraction) | Relative Volatility | | | | | | | |
|---|---|---|---|---|---|---|---|---|
| | 1.02 | 1.1 | 1.2 | 1.3 | 1.4 | 1.5 | 2.0 | 3.0 |
| | Theoretical Stages at Total Reflux | | | | | | | |
| 0.999 | 697 | 144 | 75 | 52 | 40 | 33 | 19 | 12 |
| 0.995 | 534 | 110 | 57 | 39 | 30 | 25 | 14 | 9 |
| 0.990 | 463 | 95 | 49 | 34 | 26 | 22 | 12 | 7 |
| 0.98 | 392 | 81 | 42 | 29 | 22 | 18 | 10 | 6 |
| 0.95 | 296 | 61 | 31 | 21 | 16 | 14 | 8 | 4 |
| 0.90 | 221 | 45 | 23 | 16 | 12 | 10 | 5 | 3 |

Butyraldehyde and ethanol form a minimum azeotrope boiling at 70.7° C. and containing 60.6% butyratdehyde and are thus impossible to separate by conventional distillation or rectification. Extractive distillation would be an attractive method of effecting the separation of butyraldehyde from ethanol if agents can be found that (1) will create a large apparent relative volatility between butyraldehyde and ethanol and (2) are easy to recover from these two compounds.

Table shows the relative volatility required to obtain 99% purity. With an agent giving a relative volatility of 1.9, only 20 actual plates are required.

TABLE 2

Theoretical and Actual Plates Required vs. Relative Volatility for Butyraldehyde - Ethanol Separation

| Relative Volatility | Theoretical Plates Required At Total Reflux, 99% Purity | Actual Plates Required 75% Efficiency |
|---|---|---|
| 1.35 | 31 | 42 |
| 1.7 | 17 | 23 |
| 1.9 | 15 | 20 |

OBJECTIVE OF THE INVENTION

The object of this invention is to provide a process or method of extractive distillation that will enhance the relative volatility of butyraldehyde from ethanol in their separation in a rectification column. It is a further object of this invention to identify organic compounds which in addition to the above contraints, are stable, can be separated from butyraldehyde or ethanol and recycled to the extractive column with little decomposition.

SUMMARY OF THE INVENTION

The objects of this invention are to provide a process for separating butyraldehyde from ethanol which entails the use of certain organic compounds as the agent in extractive distillation.

DETAILED DESCRIPTION OF THE INVENTION

I have discovered that certain organic compounds will greatly improve the relative volatility of butyraldehyde from ethanol and permit the separation of butyraldehyde from ethanol by rectification when employed as the agent in extractive distillation. Table 3 lists the compounds that I have found to be effective. They are dimethyl-sulfoxide, sulfolane, dimethylformamide, 1-methyl-2-pyrrolidinone, p-xylene, m-xylene, o-xylene, 1,4-dioxane, phenetol, acetal, anisole, ethyl lactate, 3-methyl-2-butanone, acetol, 1-propanol, 2-butanol, tert.amyl alcohol, 2-propanol, 1-butanol, 2-octanol, 1,2-propanediol, ethylene glycol, ethyl acetoacetate, 2,3-butanediol and dipropylene glycol.

TABLE 3

Effective Extractive Distillation Agents For Separating Butyraldehyde From Ethanol

| Compounds | Relative Volatility |
|---|---|
| Dimethylsulfoxide | 1.9 |
| Sulfolane | 1.25 |
| Dimethylformamide | 1.4 |
| 1-Methyl-2-pyrrolidinone | 1.55 |
| p-Xylene | 1.25* |
| m-Xylene | 1.9* |
| o-Xylene | 1.3* |
| 1,4-Dioxane | 1.2 |
| Phenetol | 1.25 |
| Acetal | 1.3* |
| Anisole | 1.3* |
| Ethyl lactate | 1.2 |
| 3-Methyl-2-butanone | 1.3 |
| Acetol | 1.45 |

TABLE 3-continued

Effective Extractive Distillation Agents For Separating Butyraldehyde From Ethanol

| Compounds | Relative Volatility |
| --- | --- |
| 1-Propanol | 1.5 |
| 2-Butanol | 1.5 |
| tert. Amyl alcohol | 1.25 |
| 2-Propanol | 2.1 |
| 1-Butanol | 1.35 |
| 2-Octanol | 1.3 |
| 1,2-Propanediol | 1.9 |
| Ethylene glycol | 1.35 |
| Ethyl acetoacetate | 1.25* |
| 2,3-Butanediol | 1.55 |
| Dipropylene glycol | 1.6 |

*Brings Ethanol out as overhead product.

THE USEFULNESS OF THE INVENTION

The usefulness or utility of this invention can be demonstrated by referring to the data presented in Tables 1, 2 and 3. All of the successful agents show that butyraldehyde can be separated from ethanol by means of extractive distillation in a rectification column and that the ease of separation as measured by relative volatility is considerable.

WORKING EXAMPLES

1. Ten grams of butyraldehyde, 50 grams of ethanol and 50 grams of dimethylsulfoxide were charged to a vapor-liquid equilibrium still and refluxed for three hours. Analysis indicated a vapor composition of 24.5% butyraldehyde, 75.5% ethanol; a liquid composition of 14.4% butyraldehyde, 85.6% ethanol. This is a relative volatility of butyraldehyde to ethanol of 1.9.

2. Ten grams of butyraldehyde, 40 grams of ethanol and 50 grams of m-xylene were charged to the vapor-liquid equilibrium still and refluxed for six hours. Analysis indicated a vapor composition of 15.8% butyraldehyde, 84.2% ethanol; a liquid composition 26.5% butyraldehyde, 73.5% ethanol. This is a relative volatility of ethanol to butyraldehyde of 1.9.

I claim:

1. A method for recovering butyraldehyde from a mixture consisting of butyraldehyde and ethanol which consist essentially of distilling said mixture consisting of butyraldehyde and ethanol in the presence of about one part of an extractive agent per part of butyraldehyde—ethanol mixture, recovering the butyraldehyde as overhead product and obtaining the ethanol and the extractive agent as bottoms product, wherein said extractive agent consists of one material selected from the group consisting of dimethylsulfoxide sulfolane, dimethylformamide, 1-methyl-2-pyrrolidinone, 1,4-dioxane, phenetol, ethyl lactate, 3-methyl-2-butanone, acetol, 1-propanol, 2-propanol, 1-butanol, 2-butanol, ter-t.amyl alcohol, 2-octanol, 1,2-propanediol, ethylene glycol, 2,3-butanediol and dipropylene glycol.

2. A method for recovering ethanol from a mixture consisting of ethanol and butyraldehyde which consists essentially of dispelling said mixture consisting of ethanol and butyraldehyde in the presence of about one part of an extractive agent per part of ethanol—butyraldehyde mixture, recovering the ethanol as overhead product and obtaining the butyraldehyde and the extractive agent as bottoms product, wherein said extractive agent consists of one material selected from the group consisting of p-xylene, m-xylene, o-xylene, acetal, anisole and ethyl acetoacetate.

* * * * *